United States Patent [19]

Hasegawa et al.

[11] Patent Number: 4,540,665

[45] Date of Patent: Sep. 10, 1985

[54] PROCESS FOR PRODUCING D-$\beta$-HYDROXYALKANOIC ACID

[75] Inventors: Junzo Hasegawa, Akashi; Masahiro Ogura, Ono; Hiroshi Kanema, Takasago; Hajime Kawaharada, Kakogawa; Kiyoshi Watanabe, Akashi, all of Japan

[73] Assignee: Kanegafuchi Kagaku Kogyo Kabushiki Kaisha, Osaka, Japan

[21] Appl. No.: 475,603

[22] Filed: Mar. 15, 1983

[30] Foreign Application Priority Data

Mar. 16, 1982 [JP] Japan ............................. 57-42361
Jun. 21, 1982 [JP] Japan ............................. 57-107485
Jun. 21, 1982 [JP] Japan ............................. 57-107486

[51] Int. Cl.$^3$ .................... C12P 7/42; C12P 1/02; C12N 15/00; C12N 1/32; C12N 1/14; C12N 1/16; C12R 1/72

[52] U.S. Cl. ............................ 435/146; 435/171; 435/172.1; 435/247; 435/254; 435/255; 435/921

[58] Field of Search .............. 435/146, 171, 172.1, 435/247, 254, 255, 813, 911, 921; 935/37, 59, 60, 61

[56] References Cited

U.S. PATENT DOCUMENTS

| | | | |
|---|---|---|---|
| 3,553,081 | 1/1971 | Goodhue et al. | 435/146 |
| 4,211,846 | 7/1980 | Lafferty | 435/146 |
| 4,310,635 | 1/1982 | Hasegawa et al. | 435/146 |
| 4,336,334 | 6/1982 | Powell et al. | 435/146 |

FOREIGN PATENT DOCUMENTS 2810639 9/1979 Fed. Rep. of Germany ...... 435/146
57-65188 4/1982 Japan .

OTHER PUBLICATIONS

Tahara, S. et al, *Agric. Biol. Chem.*, 42(4), pp. 879–883, 1978.
*Hackh's Chemical Dictionary*, 4th Edition, Grant, J. ed., McGraw-Hill Book Co., New York, pp. 371, 425–426, 250–251, and 117, (1969).
Chemical Abstracts, vol. 95, p. 517, Abstract No. 113347y, (1981): Tian, J. et al., "Production of Succinic Acid from the Fermentation of Liquid n–Paraffin. I. Screening and Induced Mutation of the Microorganisms".
Chemical Abstracts, vol. 95, p. 411, Abstract No. 218881w, (1981): Hasegawa, J. et al, "Studies on $\beta$-Hydroxycarboxylic acids. II. Production of $\beta$-Hydroxycarboxylic Acids from Aliphatic Carboxylic Acids by Microorganisms", J. Ferment. Technol. vol. 59, No. 4, pp. 257–262, 1981.

*Primary Examiner*—Thomas G. Wiseman
*Assistant Examiner*—Jayme A. Huleatt
*Attorney, Agent, or Firm*—Armstrong, Nikaido, Marmelstein & Kubovcik

[57] ABSTRACT

A process for producing D-$\beta$-hydroxyalkanoic acids by utilizing microorganisms having an ability of stereospecifically converting alkanoic acids, 2-alkenoic acids or alcohols into D-$\beta$-hydroxyalkanoic acids.

14 Claims, No Drawings

PROCESS FOR PRODUCING D-β-HYDROXYALKANOIC ACID

BACKGROUND OF THE INVENTION

The present invention relates to a process for producing linear D-β-hydroxyalkanoic acids, more particularly to a process for economically producing D-β-hydroxyalkanoic acids from inexpensive alkanoic acids or 2-alkenoic acids by utilizing microorganisms having an ability capable of converting the alkanoic acids or 2-alkenoic acids stereospecifically into the D-forms of β-hydroxyalkanoic acids.

D-β-hydroxyalkanoic acids are useful substances as raw materials for synthesizing optically active medicines, agricultural chemicals, perfumes and the like. In particular, the D-β-hydroxyalkanoic acid having 4 carbon atoms, i.e. D-β-hydroxybutyric acid (hereinafter referred to as "D-β-HBA"), that having 5 carbon atoms, i.e. D-β-hydroxyvaleric acid (hereinafter referred to as "D-β-HVA"), that having 6 carbon atoms, i.e. D-β-hydroxycaproic acid (hereinafter referred to as "D-β-HCA") and that having 7 carbon atoms, i.e. D-β-hydroxyheptanoic acid (hereinafter referred to as "D-β-HHA") are considered to be important.

With respect to processes for producing these D-β-hydroxyalkanoic acids, no instance in which D-β-HBA, D-β-HVA, D-β-HCA and D-β-HHA are all prepared by the same process, is reported. Since processes for producing the respective compounds except for D-β-HHA are reported, they will be explained below.

As to chemical processes, A. I. Meyers and Gerald Knaus succeeded in synthesizing D-β-HHB or D-β-HVA through chiral oxazolines as reported in Tetrahedron Letters, No. 14, 1333(1974). Also, a process for preparing ethyl eters of D-β-HBA or D-β-HVA from the corresponding β-ketoesters using an asymmetrically modified nickel catalyst is reported by A. Tai in Yukagaku, 29(11), 44(1980). Further, synthesis of D-β-HCA by enantioselective aldol condensation is reported by D. A. Evans, J. Bartroli and T. L. Shih in Journal of American Chemical Society, 103(8), 2127(1981). These chemical processes require the use of expensive chemicals, and accordingly are not suitable for the industrial production from the economical point of view.

On the other hand, the following processes are known as processes for producing D-forms of β-hydroxyalkanoic acids using microorganisms.

(1) Fermentative method: There is reported by R. M. Lafferty, as disclosed in Japanese Unexamined Patent Publication No. 18794/1978, a method for producing D-β-HBA by employing bacteria such as *Alcaligenes eutrophus* and *Bacillus megaterium* or their mutants unable to assimilate D-β-HBA with carbohydrates such as glucose or alcohols such as methanol as a carbon source. In this method, D-β-HBA is obtained as a by-product by utilizing the fact that gram positive bacteria accumulate poly-(D-β-HBA) therein, and accordingly the yield is very low. Further, the substance produced by this method is only D-β-HBA, unlike a method utilizing a β-oxidation enzyme system of fatty acids as intended by the present inventors to disclose herein.

(2) Hydrogenation method of β-ketoacids or βketoesters: There is reported a method for producing D-β-HVA, D-β-HCA or D-β-hydroxycaprylic acid ($C_8$) by stereoselective hydrogenation of β-ketoacids or β-ketoesters using Baker's yeast [R. U. Lemieux and J. Giguere, Canadian Journal of Chemistry, 29, 678(1951); György Frater, Helvetica Chimica Acta, 62, 2829(1979)]. However, β-HBA obtained by treating acetoacetic acid or ethyl acetoacetate in the same manner is the L-form. This method is not economical, since the raw materials are expensive and large amounts of Baker's yeast and sucrose are required.

(3) Microbial optical resolution method: D-β-HBA is obtained by optical resolution of DL-β-HBA using *Penicillium glaucum*, as reported by A. Mckenzie and A. Harden in Journal of Chemical Society, 83, 430(1903). This method is not only poor in optical purity, but also uneconomical for industrial production.

(4) β-Hydroxylation method of alkanoic acids or 2-alkenoic acids: It is well known as a general knowledge that decomposition of fatty acids in organisms proceeds through β-hydroxyacyl-CoA. On the basis of this knowledge, there has been made a study of production of β-hydroxyalkanoic acids from alkanoic acids or 2-alkenoic acids using microorganisms. C. T. Goodhue and J. R. Schaeffer disclose in U.S. Pat. No. 3,553,081 the production of L-β-hydroxyisobutyric acid from isobutyric acid using *Pseudomonas putida*. S. Tahara and J. Mizutani report the production of, from trans-2-alkenoic acids having 6 to 12 carbon atoms, the corresponding L-β-hydroxyalkanoic acids having 6 to 12 carbon atoms using Mucor sp. [Agricultural Biological Chemistry, 42(4), 879(1978)]. This method is considered to be the most superior as an industrial method to the before-mentioned other methods in that the raw materials are inexpensive and the mass production is relatively easy. However, β-hydroxyalkanoic acids obtained by this method are all the L-forms, and no method for producing the D-forms has been known. Thus, the present inventors searched for microorganisms capable of converting isobutyric acid or methacrylic acid into D-β-hydroxyisobutyric acid, and consequentially found the presence of microorganisms capable of producing the D-form of β-hydroxyisobutyric acid, unlike the conventional knowledge (U.S. Pat. No. 4,310,635). Further, on the basis of this finding, the present inventors carried forward a study and also found that *Candida rugosa* IFO 0750 which is a strain capable of producing D-β-hydroxyisobutyric acid can produce and accumulate D-β-HVA from valeric acid, as disclosed in Japanese Unexamined Patent Publication No. 65188/1982. However, the yield of D-β-HVA is very low. Also, production of β-hydroxyalkanoic acids from the corresponding alkanoic acids having 4, 6 or 7 carbon atoms is very trace. Although the presence of microorganisms capable of converting not only branched alkanoic acids such as isobutyric acid, but also linear alkanoic acids into D-forms of β-hydroxyalkanoic acids was found for the first time by the present inventors, it has been difficult to produce linear β-hydroxyalkanoic acids in high yields because they are easily metabolized by the microorganisms producing them.

SUMMARY OF THE INVENTION

It has now been found that when one or more mutations resulting in a reduction or elimination of the capability for metabolizing or otherwise decomposing β-hydroxyalkanoic acids are induced by treating microorganisms having an ability of producing the D-form of β-hydroxyisobutyric acid with a mutagenic agent such as N-methyl-N'-nitro-N-nitrosoguanidine (hereinafter referred to as "NTG"), the D-β-hydroxyalkanoic acids can be produced and accumulated in high yields. This mutant can also produce D-β-HBA in high yields from butyric acid, crotonic acid or such substances as being easily converted into butyric acid by the above microorganisms, e.g. butyl alcohol.

Conversion of substrates into D-β-hydroxyalkanoic acids by the mutated microorganisms of the present invention can be made by two methods. One is a method in which the mutated microorganisms are aerobically cultured in an aqueous nutrient medium containing a substrate, whereby the growth of the microorganisms and the conversion of the substrate are conducted simultaneously in one step. The other is a method in which the mutated microorganisms are previously cultured in an aqueous nutrient medium, and thereafter, a substrate is added to the resulting culture broth or to a suspension of the washed cells obtained from the broth and subsequently the mixture is incubated, preferably, aerobically incubated.

Upon producing D-β-hydroxyalkanoic acids by employing such mutants having minimal or nonexistent capability for decomposing the D-β-hydroxyalkanoic acids, it is necessary to add an adequate carbon source such as glucose or glycerol in order to supply energy necessary for conversion reaction of alkanoic acids or 2-alkenoic acids into D-β-hydroxyalkanoic acids, in addition to a carbon souce necessary for production of cells. If the addition of such a carbon source is not made, it is not possible to produce and accumulate the D-β-hydroxyalkanoic acids in high concentrations.

By the way, in case of the parent strains which are not treated for mutation, it is not necessary to add a carbon source as an energy source upon catalytic reaction of substrates with microorganisms, since they gain energy necessary for the conversion reaction in the stage of further metabolizing the produced D-β-hydroxyalkanoic acids and this energy can be utilized again in the production of the D-β-hydroxyalkanoic acids. As a matter of course, however, production of the D-β-hydroxyalkanoic acids in high yields cannot be desired.

On the basis of the finding as mentioned above, the present inventors have invented a process for producing D-forms of β-hydroxyalkanoic acids in high yields from inexpensive raw materials.

In accordance with the present invention, there is provided a process for producing a D-β-hydroxyalkanoic acid which comprises subjecting a substrate selected from the group consisting of alkanoic acids, 2-alkenoic acids and 1-alkanols aerobically to the action of a mutant of a microorganism having an ability of converting a linear alkanoic acid or 2-alkenoic acid into the corresponding D-β-hydroxyalkanoic acid in the presence of an energy source, said mutant having minimal or nonexistent capability for decomposing said D-β-hydroxyalkanoic acid, and recovering the produced D-β-hydroxyalkanoic acid.

DETAILED DESCRIPTION

Microorganisms belonging to any genera and species, including microorganisms of Candida genus such as Candida rugosa IFO 0750, Candida rugosa IFO 0591 and Candida parapsilosis IFO 0708, can be employed as parent strains used for inducing mutants having minimal or nonexistent capability for decomposing D-β-hydroxyalkanoic acids, so far as they have an ability of converting alkanoic acids or 2-alkenoic acids into the D-β-hydroxyalkanoic acids. The term "IFO" indicates the depository "Institute for Fermentation, Osaka" (Jaso Nishimachi, Higashi-Yodogawaku, Osaka, Japan).

The present invention will be described by reference to a process in which Candida rugosa IFO 0750 is employed as a parent strain, and a mutant is obtained therefrom and D-β-hydroxyalkanoic acids are produced by employing the mutant, but mutants can also be obtained in the same manner from other microorganisms and the production of the D-β-hydroxyalkanoic acids is possible.

The mutants can be obtained in a usual manner, for instance, by conducting a mutation treatment by means of a chemical method using a mutagenic agent such as NTG or a physical method such as ultraviolet irradiation, and collecting the mutants unable to assimilate D-β-hydroxyalkanoic acids. Microorganisms unable to assimilate d-β-hydroxyalkanoic acids can also be obtained by selecting a colony which does not grow on a plate containing the corresponding β-hydroxyalkanoic acids as the sole carbon source. Although the obtainment of the mutant as shown herein is made by selecting a mutant unable to assimilate butyric acid, mutants suited for the purpose can also be obtained by selecting strains unable to assimilate valeric acid, caproic acid or heptanoic acid.

Linear alkanoic and 2-alkenoic acids, particularly those having 4 to 7 carbon atoms are used as substrates used in the conversion reaction. 1-Alkanols convertible easily into the corresponding alkanoic acids by the used mutant can also be used as substrates. That is to say, according to the present invention, D-β-HBA can be produced from butyric acid, crotonic acid or butyl alcohol, D-β-HVA can be produced from valeric acid, 2-pentenoic acid or amyl alcohol, D-β-HCA can be produced from caproic acid, 2-hexenoic acid or hexyl alcohol, and D-β-HHA can be produced from heptanoic acid, 2-heptenoic acid or heptyl alcohol.

The conversion reaction of a substrate by the mutant for producing a D-β-hydroxyalkanoic acid can be carried out by the following two methods. In one method, the substrate is added to an aqueous medium from the beginning of the culture, and the mutant is cultured, whereby the production of cells and the reaction are simultaneously conducted. In the other method, the mutant is previously cultured in an aqueous nutrient medium, and the substrate is added to the obtained culture broth or an aqueous suspension of cells collected from the culture broth and is reacted. The cell suspension is prepared by separating the cells from the obtained culture broth and suspending the cells in water, a buffer or an aqueous nutrient medium. In the above both methods, for producing the D-β-hydroxyalkanoic acids in high concentrations, it is necessary to add a carbon source that microorganisms can utilize, e.g. glucose, glycerol, acetic acid, its salts or ethanol, to the reaction system as an energy supply source for the reaction. In particular, in case of the latter method in which the production of the cells and the reaction are separately carried out, the production of the D-β-hydroxyalkanoic acid is trace if a carbon source is not supplied as an energy source.

For culture of mutants, any media in which they can grow can be employed. The media usually contain a carbon source and a nitrogen source, and if necessary, a mineral source, and so on. Any carbon sources that the mutants can utilize are usable, e.g. carbohydrates such as glucose and molasses, organic acids such as acetic acid, and alcohols such as ethanol and glycerol. The nitrogen source includes inorganic and organic compounds such as ammonium sulfate, ammonium chloride, ammonium phosphate, aqueous ammonia, urea, amino acids, pepton, and hydrolysates of soybean protein. The mineral source includes, for instance, inorganic acid salts or potassium, magnessium, zinc, iron, manganese, copper and calcium. If necessary, yeast extract, meat extract, corn steep liquor or vitamines may be added to the medium.

The culture is aerobically carried out at a temperature of 20° to 45° C. and a pH of 6 to 9 for 1 to 10 days. A microorganism grows in the early stage of the culture and the production of D-$\beta$-hydroxyalkanoic acid starts from the middle of the culture. After the completion of the cell production, a carbon source such as glucose is added as an energy source continuously or intermittently to the reaction system, whereby the production of the D-$\beta$-hydroxyalkanoic acid proceeds and the D-$\beta$-hydroxyalkanoic acid is accumulated in high concentrations. The substrate may be added to the medium either in the early stage of the culture or after the growth of the microorganism.

The recovery of the produced D-$\beta$-hydroxyalkanoic acid from the culture broth or the reaction mixture is carried out by a usual method for recoverying hydroxy acids, e.g. ion exchange or solvent extraction. A solvent extraction method will be shown as an instance for recoverying the product. After removing the cells from the culture broth or the reaction mixture, the supernatant liquid is concentrated, and is acidified with a mineral acid such as sulfuric acid or hydrochloric acid, preferably to pH 2.5. The acidified liquid is then extracted with a hydrophobic solvent such as ethyl ether, butanol, methyl isobutyl ketone or ethyl acetate, and after removing the solvent, the residue is distilled under reduced pressure, thus obtaining the D-$\beta$-hydroxyalkanoic acid. Also, an alkyl ester of the D-$\beta$-hydroxyalkanoic acid can be obtained in good yields by treating the crude extract containing the D-$\beta$-hydroxyalkanoic acid to convert into the alkyl ester thereof such as methyl ester or ethyl ester and then conducting the distillation under reduced pressure.

The determination of the amount of the produced D-$\beta$-hydroxyalkanoic acids can be carried out by gas chromatography using a glass column packed with Shimadzu FAL-M 10%/Shimalite [Junzo Hasegawa et al, Journal of Fermentation Technology, 59, 203(1981)].

The present invention is more specifically described and explained by means of the following Examples. It is to be understood that the present invention is not limited to the Example, and various changes and modifications may be made in the invention without departing from the spirit and scope thereof.

In the following Examples, media having the following compositions were employed.

S-Medium: glucose 40 g., $(NH_4)_2HPO_4$ 13 g., $KH_2PO_4$ 7 g., $MgSO_4.7H_2O$ 0.8 g., $ZnSO_4.7H_2O$ 60 mg., $FeSO_4.7H_2O$ 90 mg., $CuSO_4.5H_2O$ 5 mg., $MnSO_4.4H_2O$ 10 mg., NaCl 0.1 g., biotin 1 mg., thiamine-HCl 2 mg., water 1 liter, pH 7.2

S-Medium plate: S-medium + Agar 20 g.

C-Medium plate: glucose 20 g., yeast extract 5 g., meat extract 10 g., pepton 10 g., agar 20 g., water 1 liter, pH 7.0

D-Medium plate: the same as the S-medium except that 10 g. of butyric acid was used instead of glucose and the pH was adjusted to 7.0 with NaOH P-Medium: the same as the S-medium except that 5 g. of yeast extract was used instead of biotin and thiamine-HCl; pH 7.2

The mutant used in the Examples was obtained as follows:

*Candida rugosa* IFO 0750 was inoculated in 30 ml. of S-medium placed in a 500 ml. flask, and aerobically cultured at 30° C. for 20 hours. After washing 1.5 ml. of the thus obtained culture broth with 0.5M phosphate buffer (pH 7.0) 3 times, it was suspended in 3 ml. of a 0.5 mg./ml. NTG solution and the suspension was allowed to stand at 4° C. for 60 minutes. The suspension was then washed with 0.5M phosphate buffer (pH 7.0) 3 times and was spread onto the C-medium plate, and the culture was conducted at 30° C. for 2 days. The colonies which appeared on the plate were replicated onto the S-medium plate and the B-medium plate, and cultured at 30° C. for 3 days, thereby selecting the colonies which grows on the S-medium plate but does not grow on the B-medium plate.

The thus obtained mutants unable to assimilate butyric acid were inoculated in 30 ml. of a medium prepared by adding butyric acid to the S-medium in a concentration of 2% and adjusting to pH 7.2 and placed in a 500 ml. flask, and was cultured at 30° C. for 2 to 4 days with shaking. It was confirmed by analyzing the production of D-$\beta$-HBA in the thus obtained culture broth by the method mentioned before that the mutant (*Candida rugosa* KT 8202) capable of producing D-$\beta$-HBA in high yields from butyric acid was obtained. The properties of the mutant were as shown in Table 1.

TABLE 1

|  | Parent (IFO 0750) | Mutant (KT 8202) |
| --- | --- | --- |
| Assimilation |  |  |
| Glucose | +++ | +++ |
| Butyric acid | +++ | − |
| D-$\beta$-HBA | +++ | − |
| L-$\beta$-HBA | +++ | − |
| D-$\beta$-HVA | ++ | − |
| D-$\beta$-HCA | + | − |
| D-$\beta$-HHA | + | − |

(Note)
+++: Well growth
−: Non growth

*Candida rugosa* KT 8202 is deposited as FERM BP-111 in Fermentation Research Institute, Agency of Industrial Science and Technology of 1-3, Higashi 1-chome, Yatabe-machi, Tsukuba-gun, Ibaraki-ken, 305, Japan.

EXAMPLE 1

An alkanoic acid was added to the P-medium in an amount shown in Table 2. The medium was adjusted to pH 7.2 with NaOH, and a 30 ml. portion thereof was placed in a 500 ml. flask and was sterilized at 121° C. for 20 minutes. *Candida rugosa* IFO 0750 (parent) or *Candida rugosa* KT 8202 (mutant) was inoculated into the medium, and then cultured at 30° C. for 72 to 120 hours with shaking. During the culture, the medium was maintained at pH 7.0 with an aqueous solution of NaOH, and a 2% glucose solution was added to the medium every day. The produced D-$\beta$-hydroxyalkanoic acid was analyzed by gas chromatography. The results are shown in Table 2.

TABLE 2

| Strain | Alkanoid acid (v/v %) | Culture period (hour) | D-$\beta$-Hydroxy-alkanoic acid produced (mg./ml.) | |
| --- | --- | --- | --- | --- |
| Parent | 2% Butyric acid | 120 | D-$\beta$-HBA | trace |

TABLE 2-continued

| Strain | Alkanoid acid (v/v %) | Culture period (hour) | D-β-Hydroxy-alkanoic acid produced (mg./ml.) | |
|---|---|---|---|---|
| Mutant | 2% Butyric acid | 120 | D-β-HBA | 13.0 |
| Parent | 1% Valeric acid | 72 | D-β-HVA | trace |
| Mutant | 1% Valeric acid | 72 | D-β-HVA | 6.5 |
| Parent | 0.5% Caproic acid | 72 | D-β-HCA | trace |
| Mutant | 0.5% Caproic acid | 72 | D-β-HCA | 4.4 |
| Parent | 0.5% Heptanoic acid | 72 | D-β-HHA | trace |
| Mutant | 0.5% Heptanoic acid | 72 | D-β-HHA | 2.5 |

From 2 liters of each culture broth obtained by culture under the same condition as above, cells were removed by centrifugation and the culture broth was concentrated to 400 to 500 ml. and adjusted to pH 2 with sulfuric acid. It was then extracted with three 500–700 ml. portions of ethyl acetate, and the solvent was distilled away under reduced pressure to give a colorless oily material. The thus obtained each oily material was identified as D-β-HBA, D-β-HVA, D-β-HCA or D-β-HHA by NMR, gas chromatography, IR analysis. The specific optical rotation of the products were also measured. The results are shown in Table 3.

TABLE 3

| | Boiling point (°C./mm Hg) | $[\alpha]_D^{25}$ (conc., solvent) |
|---|---|---|
| D-β-HBA | 127/18 | −23.0° (6.1, H$_2$O) |
| D-β-HVA | 95/3 | −26.9° (4, CHCl$_3$) |
| D-β-HCA | 114/2 | −27.5° (2, CHCl$_3$) |
| D-β-HHA | 126/1 | −25.8° (2, CHCl$_3$) |

EXAMPLE 2

After placing 30 ml. of the P-medium in a 500 ml. flask and sterilizing it, *Candida rugosa* KT 8202 was inoculated in the medium and cultured at 30° C. for 23 hours with shaking. To the obtained culture broth was added a 2-alkenoic acid or 1-alkanol in a concentration shown in Table 4, and the broth was adjusted to pH 7.0 with a NaOH solution. The reaction was carried out at 30° C. for 48 to 96 hours, while adding 600 mg. of glucose per day to the reaction mixture and maintaining at pH 7.0. After the incubation, the produced D-β-hydroxyalkanoic acid was analyzed by gas chromatography. The results are shown in Table 4.

TABLE 4

| Substrate | Culture period (hour) | D-β-Hydroxyalkanoic acid produced (mg./ml.) | |
|---|---|---|---|
| 2% Crotonic acid | 96 | D-β-HBA | 5.8 |
| 2% Butyric anhydride | " | " | 4.6 |
| 1% Butyl alcohol | " | " | 6.2 |
| 0.5% Butyl aldehyde | " | " | 2.9 |
| 1% 2-Pentenoic acid | 96 | D-β-HVA | 3.3 |
| 1% Amyl alcohol | " | " | 3.2 |
| 0.5% 2-Hexenoic acid | 48 | D-β-HCA | 2.9 |
| 0.5% Hexyl alcohol | " | " | 0.7 |
| 0.5% 2-Heptenoic acid | 48 | D-β-HHA | 1.8 |
| 0.5% Heptyl alcohol | " | " | 0.4 |

EXAMPLE 3

After placing 30 ml. of the P-medium in a 500 ml. flask and sterilizing it, *Candida rugosa* KT 8202 was inoculated in the medium and cultured at 30° C. for 24 hours. Cells were collected by centrifuging the obtained culture broth, washed with 0.5M phosphate buffer (pH 7.0), and suspended in the same buffer to give 30 ml. of the cell suspension. To the suspension was added an alkanoic acid in an amount shown in Table 5. The reaction was carried out at 30° C., while adding glucose (600 mg./24 hours) or acetic acid (0.3 ml./12 hours) to the system and maintaining the system at pH 7.0. The amounts of the D-β-hydroxyalkanoic acids produced in the reaction mixtures after the completion of the reaction were as shown in Table 5, respectively.

TABLE 5

| Substrate | Energy source | D-β-Hydroxy-alkanoic acid produced (mg./ml.) |
|---|---|---|
| 2% Butyric acid | none | 0.6 |
| | glucose | 14.0 |
| | glycerol | 13.0 |
| | acetic acid | 6.5 |
| | ethanol | 6.3 |
| 1% Valeric acid | none | 0.3 |
| | glucose | 6.4 |
| | glycerol | 6.1 |
| | acetic acid | 4.0 |
| | ethanol | 3.5 |
| 0.5% Caproic acid | none | 0.1 |
| | glucose | 4.3 |
| | glycerol | 4.1 |
| | acetic acid | 1.8 |
| | ethanol | 2.0 |
| 0.5% Heptanoic acid | none | 0.1 |
| | glucose | 2.4 |
| | glycerol | 2.3 |
| | acetic acid | 1.2 |
| | ethanol | 1.4 |

In addition to the ingredients used in the Examples, other ingredients can be used in the Examples as set forth in the specification to obtain substantially the same results.

What we claim is:

1. A process for producing a D-β-hydroxyalkanoic acid which comprises subjecting a substrate selected from the group consisting of an alkanoic acid, a 2-alkenoic acid and a 1-alkanol aerobically in a liquid medium to the action of a mutant of a microorganism belonging to the genus Candida in the presence of a sufficient amount of a carbon source to supply energy necessary for a conversion reaction, thereby converting the substrate into the corresponding D-β-hydroxyalkanoic acid, said Candida mutant being substantially unable to decompose the D-β-hydroxyalkanoic acid, and recovering the produced D-β-hydroxyalkanoic acid from the liquid medium.

2. The process of claim 1, wherein said Candida mutant is *Candida rugosa* KT 8202 (FERM BP-111).

3. The process of claim 1, wherein said mutant is derived from *Candida rugosa* IFO 0750.

4. The process of claim 1, wherein said mutant is derived from *Candida rugosa* IFO 0591.

5. The process of claim 1, wherein said mutant is derived from *Candida parapsilosis* IFO 0708.

6. The process of claim 1, wherein the substrate is subjected to the action of the mutant in a culture broth obtained by cultivating the mutant in an aqueous nutrient medium aerobically at a temperature of 20° to 45° C. and a pH of 6 to 9 for 1 to 10 days.

7. The process of claim 1, wherein the substrate is subjected to the action of the mutant in a cell suspension prepared by cultivating the mutant in an aqueous nutrient medium aerobically at a temperature of 20° to 45° C.

and a pH of 6 to 9 for 1 to 10 days, separating cells from the obtained culture broth and suspending the separated cells in water, a buffer solution or an aqueous nutrient medium.

8. The process of claim 1, wherein said alkanoic acid is a member selected from the group consisting of butyric acid, valeric acid, caproic acid and heptanoic acid.

9. The process of claim 1, wherein said 2-alkenoic acid is a member selected from the group consisting of crotonic acid, 2-pentenoic acid, 2-hexenoic acid and 2-heptenoic acid.

10. The process of claim 1, wherein said 1-alkanol is a member selected from the group consisting of butyl alcohol, amyl alcohol, hexyl alcohol and heptyl alcohol.

11. The process of claim 1, wherein said produced D-$\beta$-hydroxyalkanoic acid is a member selected from the group consisting of D-$\beta$-hydroxybutyric acid, D-$\beta$-hydroxyvaleric acid, D-$\beta$-hydroxycaproic acid and D-$\beta$-hydroxyheptanoic acid.

12. The process of claim 1, wherein said carbon source is a member selected from the group consisting of glucose, glycerol, ethanol and acetic acid.

13. The process of claim 1, wherein the produced D-$\beta$-hydroxyalkanoic acid is recovered by extracting the acidified reaction mixture with a hydrophobic solvent.

14. The process of claim 13, wherein said hydrophobic solvent is a member selected from the group consisting of ethyl acetate, ethyl ether, butanol and methyl isobutyl ketone.

* * * * *